Figure 1:
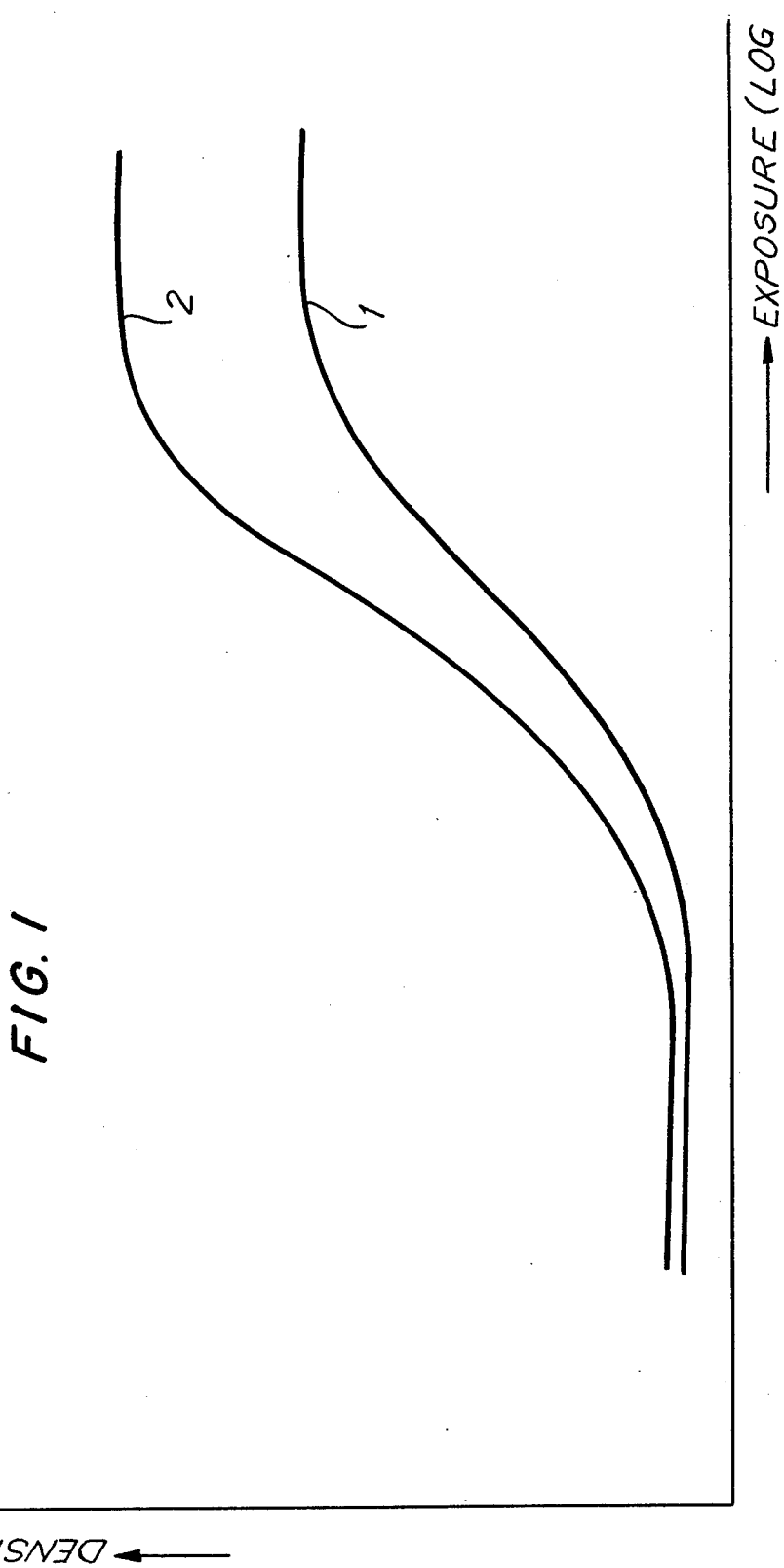

United States Patent [19]

Fujimatsu et al.

[11] 4,008,086

[45] Feb. 15, 1977

[54] SILVER HALIDE EMULSION CONTAINING PHOTOGRAPHIC YELLOW COUPLER

[75] Inventors: Wataru Fujimatsu; Shui Sato, both of Hachioji; Tamotsu Kojima, Kokubunji; Takaya Endo, Hino; Kazumi Minahara, Hachioji, all of Japan

[73] Assignee: Konishiroku Photo Industry Co., Ltd., Tokyo, Japan

[22] Filed: May 16, 1975

[21] Appl. No.: 578,017

Related U.S. Application Data

[62] Division of Ser. No. 351,031, April 13, 1973, Pat. No. 3,900,483.

[30] Foreign Application Priority Data

Apr. 15, 1972 Japan ............................ 47-37367
May 27, 1972 Japan ............................ 47-52179

[52] U.S. Cl. .............................. 96/56.5; 96/29 D; 96/100
[51] Int. Cl.² ..................... G03C 7/00; G03C 1/40
[58] Field of Search ............... 96/100, 56.2, 56.5, 96/100 N

[56] References Cited

UNITED STATES PATENTS 3,900,483  8/1975  Fujimatsu et al. .................. 96/100

*Primary Examiner*—J. Travis Brown
*Attorney, Agent, or Firm*—Bierman & Bierman

[57] ABSTRACT

An improved photographic system in which a new yellow coupler is employed. The yellow coupler has the formula,

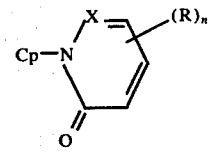

wherein X is a —N= or —CH= group; Cp is a residue formed by removing one hydrogen atom of the active methylene group of an acetanilide yellow coupler; $n$ is an integer of 1 to 4; and R is a hydrogen or halogen atom, or an alkyl, alkoxy, alkylcarbonyl, aryl, arylcarbonyl, amino, acylamino, carboxyl, nitrile, aralkyl or aralkyloxy group, provided that in case $n$ is 2 or more the R groups may be the same or different, and two adjacent R groups in combination may form a benzene ring.

11 Claims, 2 Drawing Figures

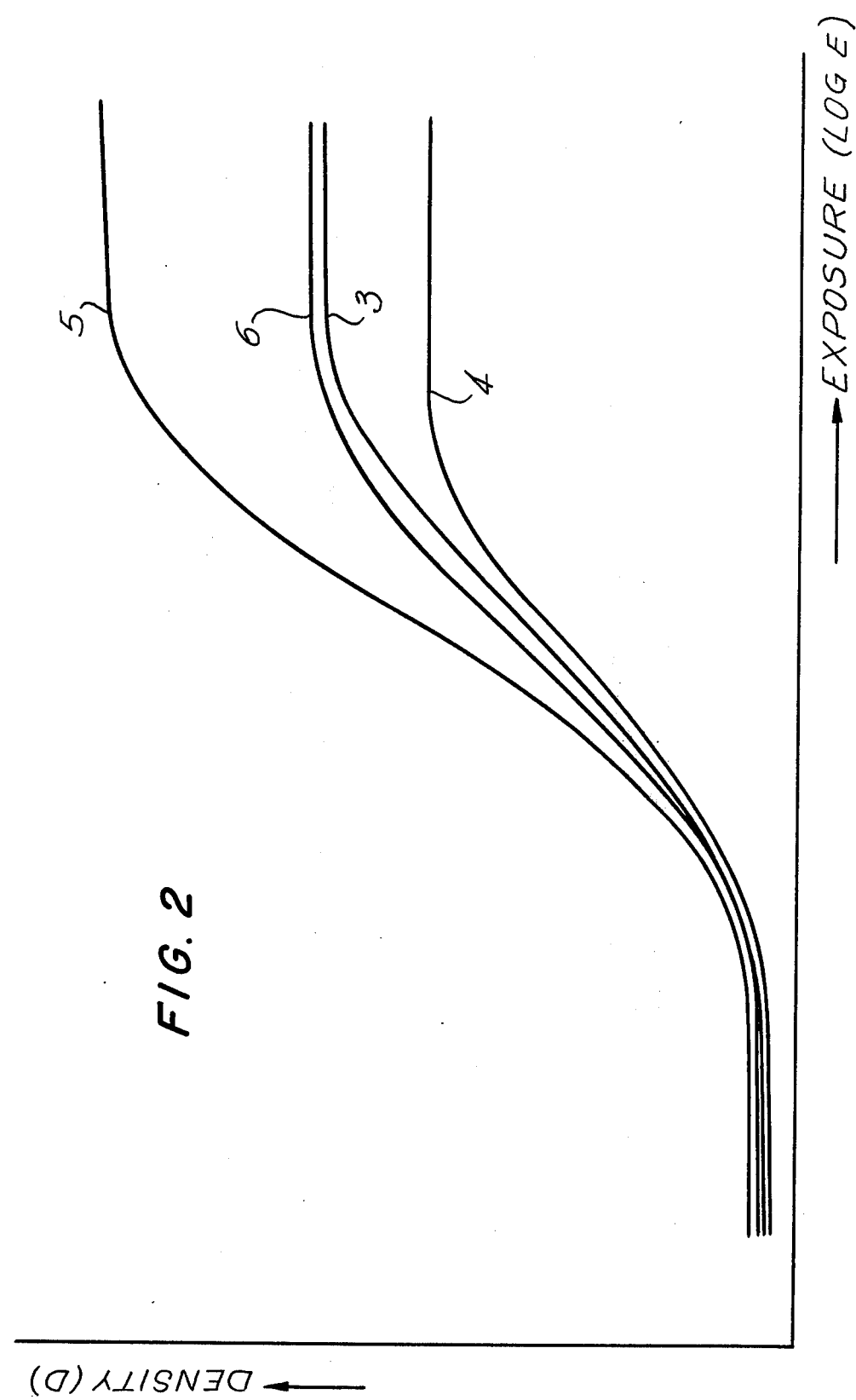

SILVER HALIDE EMULSION CONTAINING PHOTOGRAPHIC YELLOW COUPLER

This application is a Divisional Application of Ser. No. 351,031, filed Apr. 13, 1973, now U.S. Pat. No. 3,900,483, issued Aug. 19, 1975.

This invention relates to a novel coupler for forming a yellow image which is used in color photography.

It is well known that in color photography, a coupler-containing light-sensitive photographic material, for example, is exposed and then color-developed with a developer containing an aromatic primary amine type developing agent as a main ingredient to form a dye image. Among the couplers used in said photography, the yellow coupler has an active methylene group which serves to form a yellow dye by coupling with an oxidation product of the aromatic primary amine type developing agent. In case the said active methylene group has not been substituted, i.e. in the case of an unsubstituted type yellow coupler, 4 molecules of silver halide is required in order to form one molecule of dye in the color development. For this reason, the above-mentioned yellow coupler is called a 4-equivalent yellow coupler.

On the other hand, it is well known that the same dye as in the case of the unsubstituted type coupler can be formed also from a so-called substituted type yellow coupler, i.e. a yellow coupler having an active methylene group, one of the hydrogen atoms of which has been substituted by a substituent such as a chlorine atom or the like halogen atom. In this case, the halogen atom or the like substituent is released in the course of the color development reaction, and one molecule of dye can be formed from 2 molecules of developed silver halide. For this reason, such substituted type yellow coupler as mentioned above is called a 2-equivalent yellow coupler.

This 2-equivalent yellow coupler has advantages over the 4-equivalent coupler such as mentioned below.

1. The 2-equivalent yellow coupler is higher in coupling rate than the 4-equivalent yellow coupler, and hence is successfully usable in high temperature quick processing, particularly in 3-bath processing comprising only the steps of development, bleaching, fixing and water-washing.

2. The amount of silver halide required for forming a dye may be one half the amount required in the case of the 4-equivalent coupler, so that the production cost of the photographic material can be reduced.

3. The emulsion layer can be made thinner to improve the resulting color image in resolution and sharpness.

4. In the case of a multi-layered photographic material, the transmission of light to the lower layers is enhanced to improve the photographic material in photographic speed.

In view of the above-mentioned advantages, the substituted type yellow coupler is extremely advantageous for use in photography. On the other hand, the conventional substituted type yellow coupler has the disadvantages that it tends to form fog or the like color stains and tends to disturb the development of photographic material.

In contrast to the conventional substituted type yellow coupler mentioned above, the substituted type yellow coupler according to the present invention is colorless, is high in reactivity and scarcely forms color stains. Moreover, the yellow dye formed by the aforesaid color development is excellent in fastness to light, humidity, heat and pressure, has no unnecessary absorptions in the long wavelength area, shows less and sharp absorptions in the green light area, and has a color tone quite favorable for color reproduction.

The substituted type photographic yellow coupler according to the present invention is represented by the formula,

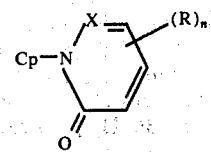

wherein X is a —N= or —CH= group; $C_p$ is a residue formed by removing one hydrogen atom of the active methylene group of a yellow coupler having an active methylene group; n is an integer of 1 to 4; and R is a hydrogen or halogen atom, or an alkyl, alkoxy, alkylcarbonyl, aryl, arylcarbonyl, amino, acylamino, carboxyl, nitrile, aralkyl or aralkyloxy group, provided that in case n is 2 or more, R's may be the same or different, and two adjacent R's in combination may form a benzene ring. The coupler according to the present invention is characterized by having as a substituent in the active point thereof 2 (1H)-pyridone or 3(2H)-pyridazone having or not having substituted groups. Typical examples of the said substituents are as follows:

2(1H)-Pyridone
3-Chloro-2(1H)-pyridone
5-Bromo-2(1H)-pyridone
3-Fluoro-2(1H)-pyridone
3,5-Dichloro-2(1H)-pyridone
5-Acetamide-2(1H)-pyridone
5-Chloro-2(1H)-pyridone
3,5-Dibromo-2(1H)-pyridone
5-Benzoyl-2(1H)-pyridone
5-Acetyl-2(1H)-pyridone
5-Benzoyl-3-bromo-2(1H)-pyridone
5-p-Ethylbenzoly-2(1H)-pyridone
3-Bromo-4-ethoxy-2(1H)-pyridone
5-p-Chlorobenzoyl-2(1H)-pyridone
3-Ethyl-2(1H)-pyridone
4-Methoxy-2(1H)-pyridone
3-Methyl-2(1H)-pyridone
3,5-Dimethyl-2(1H)-pyridone
5-Bromo-3-methyl-2(1H)-pyridone
4-Acetyl-2(1H)-pyridone
5-Ethyl-4-methyl-2(1H)-pyridone
3,4,5,6-Tetrachloro-2(1H)-pyridone
4-Butoxy-2(1H)-quinolone
3-Methyl-2(1H)-quinolone
4-Methyl-6-phenyl-2(1H)-quinolone
3,4-Dimethyl-2(1-quinolone
4-Phenyl-2(1)-quinolone
3-Phenyl-2(1H)-quinolone
3Hexyl-2(1H)-quinolone
4-Carboxylic acid-2(1H)-quinolone
4-Benzyloxycarbonyl-2(1H)-quinolone
3(2H)-Pyridazone
4,5-Dibromo-3(2H)-pyridazone
4,5-Dichloro-3(2)-pyridazone
6-p-Bromoanilino-3(2H)-pyridazone
4-Methyl-3-(2H)-pyridazone 4-Methyl-5-ethyl-3(2H)-pyridazone
6-Ethoxy-3(2H)-pyridazone
4,6-Dimethyl-3(2H)-pyridazone
6-Phenyl-3(2H)-pyridazone
4,6-Diphenyl-3(2H)-pyridazone
4,5-Diphenoxy-3(2H)-pyridazone
5-Methyl-6-ethoxy-3(2H)-pyridazone
4-Chloro-3(2H)-pyridazone
6-Chloro-5-phenyl-(2H)-pyridazone   6-Benzyl-5-phenyl-3(2H)-pyridazone
4-Acetamide-3(2H)-pyridazone
5-Benzamide-4-chloro-3(2H)-pyridazone
4-Benzoyl-5,6-diphenyl-3(2H)-pyridazone
6-Butoxy-3(2H)-pyridazone
4-Acetyl-5,6-diphenyl-3(2H)-pyridazone
6-Bromo-3(2H)-pyridazone
6-Benzyloxy-3(2H)-pyridazone
5-Bromo-4-chloro-3(2H)-pyridazone
5-Bromo-6-phenyl-3(2H)-pyridazone
6-Chloro-4-methyl-3(2H)-pyridazone
6-n-Octyl-3(2H)-pyridazone
4-Chloro-5-amino-3(2H)-pyridazone
6-(p-Chlorophenyl)-3(2H)-pyridazone Yellow couplers, in which the above-mentioned substituents have been substituted in the active points thereof, may be any of those which have active methylene groups in the molecules. When these substituents are substituted in the active points of couplers, such excellent properties as mentioned previously can be imparted to the couplers.

Typical examples of the yellow couplers according to the present invention are shown below, but yellow couplers according to the present invention are not limited to these.

(A-1)  α-[2(1H)-Pyridone]-α-pivalylacetanilide

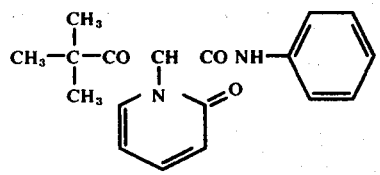

(A-2)  α-[2(1H)-Pyridone]-α-pivalyl-2,5-dichloroacetanilide

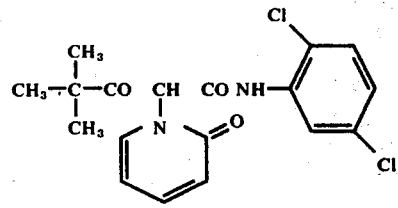

(A-3)  α-[2(1H)-Pyridone]-α-pivalyl-2-chloro-5-(γ-2,4-di-t-amylphenoxybutyramide)-acetanilide

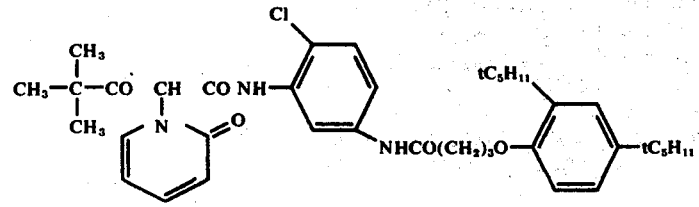

(A-4)  α-[5-Chloro-2(1H)-pyridone]-α-pivalyl-2-chloro-5-[γ-(2,4-di-t-amylphenoxy)butyramide]-acetanilide

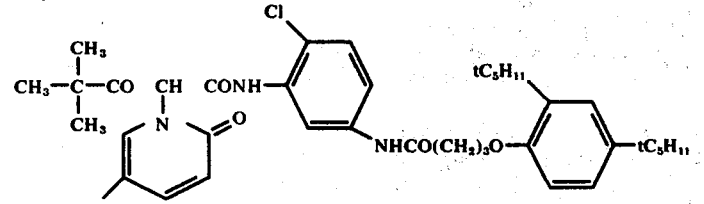

(A-5)  α-[3-Chloro-2(1H)-pyridone]-α-benzoylacetanilide

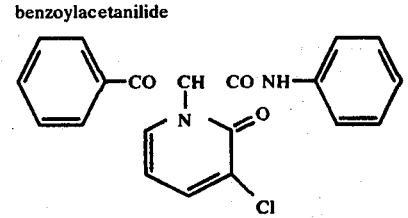

(A-6)  α-[2(1H)-Pyridone]-α- 3-[α-(2,4-di-t-amylphenoxy)-butyramide]-benzoyl -2-methoxyacetanilide

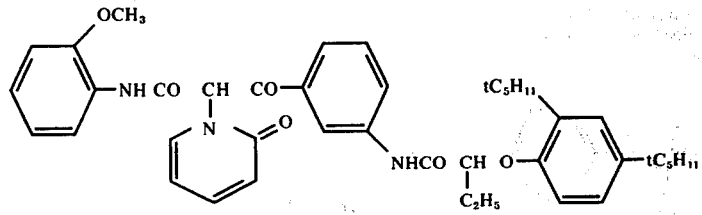

(A-7) α-[2(1H)-Pyridone)]-α-octadecyloxybenzoyl-3,5-dicarboxyacetanilide dipotassium salt

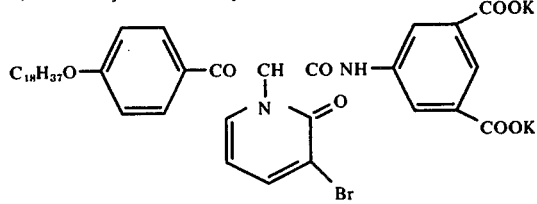

(A-8) α-[3,5-Dibromo-2(1H)-pyridone]-α- 3-[α-(2,4-di-t-amylphenoxy)-butyramide]-benzoyl -2-methoxyacetanilide

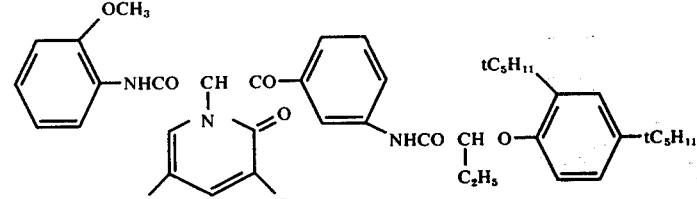

(A-9) α-[3-Nitrile-2(1H)-pyridone]-α-pivalyl-2-chloro-5-[γ-(2,4-di-t-amylphenoxy)-butyramide]-acetanilide

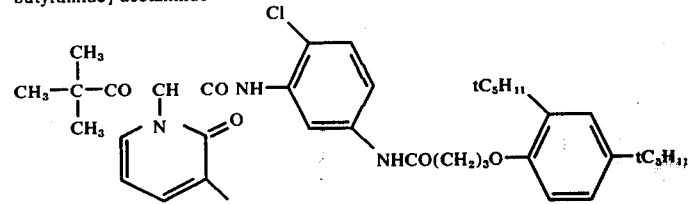

(A-10) α-[3-Bromo-2(1H)-pyridone]-α-benzoyl-acetanilide

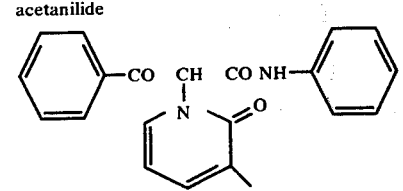

(A-11) α-[3-Bromo-2(1H)-pyridone]-α-pivalyl-2-chloro-5-[γ-(2,4-di-t-amylphenoxy)-butyramide]-acetanilide

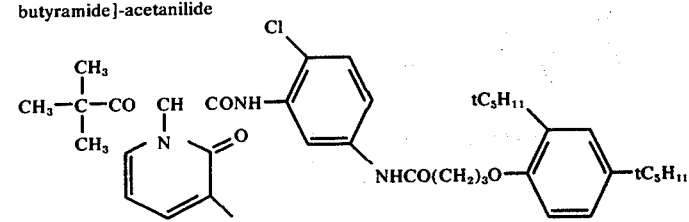

(A-12) α-[5-Bromo-2(1H)-pyridone]-α-pivalyl-2,5-dichloroacetanilide

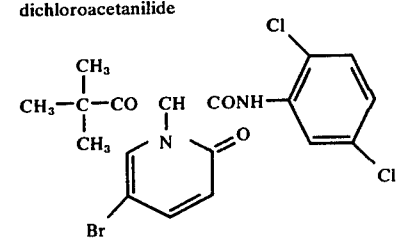

(A-13) α-[5-Bromo-2(1H)-pyridone]-α- 3-[α-(2,4-di-t-amylphenoxy)-butyramide]-benzoyl-2-methoxyacetanilide

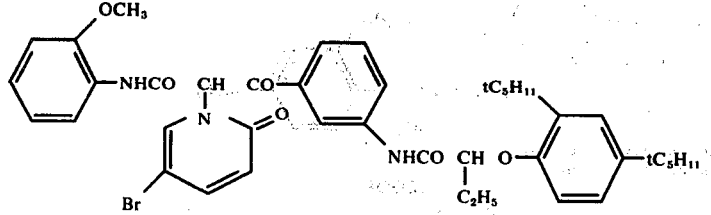

(A-14) α-[4-Ethyl-2-(1H)-pyridone]-α-pivalyl-acetanilide

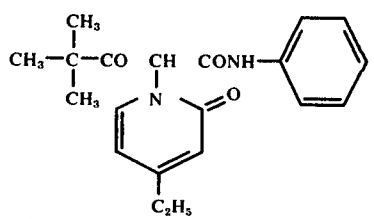

(A-15) α-[5-(p-Ethylbenzoyl)-2(1H)-pyridone]-α-pivalylacetanilide

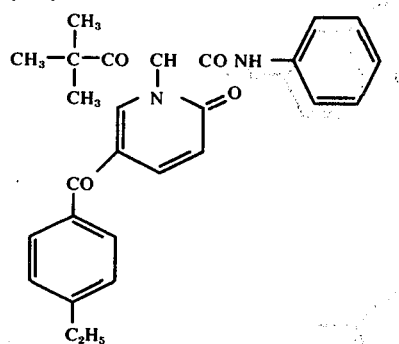

(A-16) α-[3,5-Dichloro-2(1H)-pyridone]-α- 3-[α-(2,4-di-t-amylphenoxy)-butyramide]-benzoyl -2-methoxyacetanilide

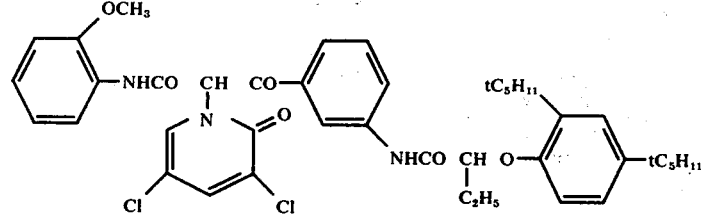

(A-17) α-[5-Bromo-2(1H)-pyridone]-α-pivalyl-2-chloro-5-[γ-(2,4-di-t-amylphenoxy)-butyramide]-acetanilide

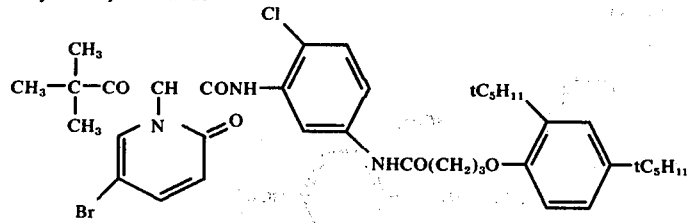

(A-18) α-[4-Ethyl-2(1H)-pyridone]-α-benzoyl-acetanilide

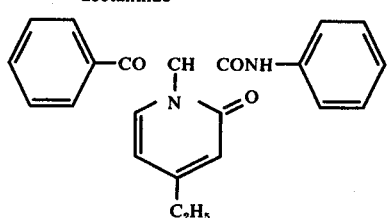

(A-19) α-[4-Methyl-2(1H)-pyridone]-α-pivalylacetanilide

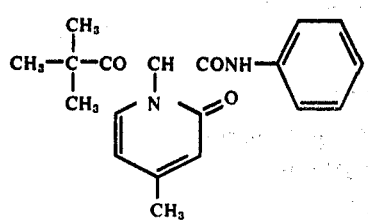

(A-20) α-[4-Carboxylic acid-2(1H)-quinolone]-
α-pivalyl-2-chloro-5-[γ-(2,4,-di-t-
amylphenoxy)-butyramide]-acetanilide

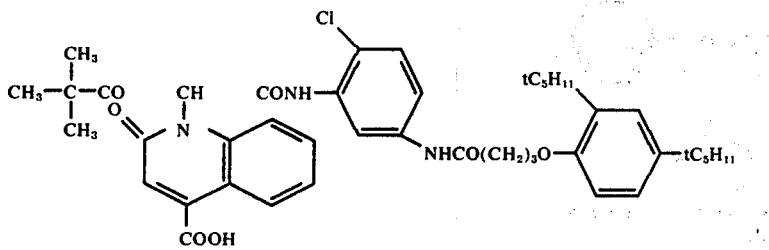

(B-1) α-[3-(2H)-Pyridazone]-α-pivalyl-
acetanilide

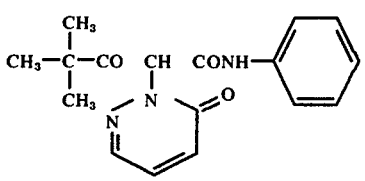

(B-2) α-[3(2H)-Pyridazone]-α-benzoyl-
acetanilide

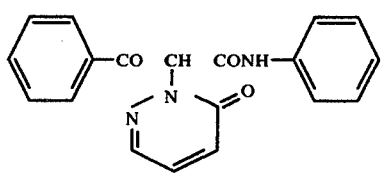

(B-3) α-[3(2H)-Pyridazone]-α-pivalyl-2-
chloro-5-[γ-(2,4-di-t-amylphenoxy)-
butyramide]-acetanilide

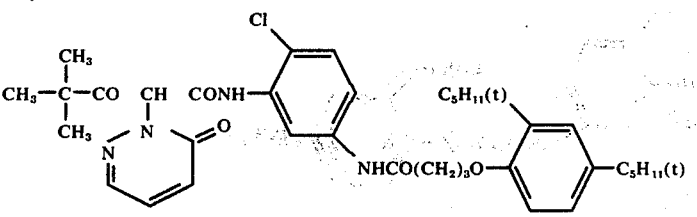

(B-4) α-[4,5-Dibromo-3(2H)-pyridazone]-α-
benzoyl-2-chloro-5-[γ-(dodecyloxycarbonyl)-
ethoxycarbonyl]-acetanilide

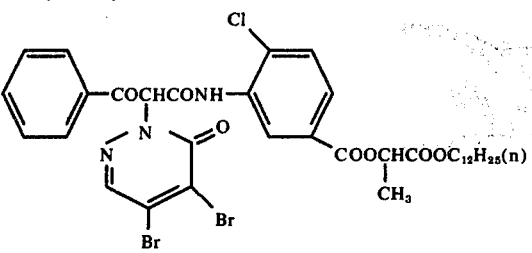

(B-5) α-[4,5-Dichloro-3(2H)-pyridazone]-α-pivalyl-
2-chloro-5-[γ-(2,4-di-t-amylphenoxy)-
butyramide]-acetanilide

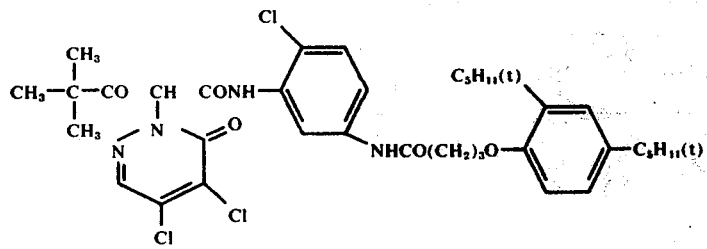

(B-6) α-[4,5-Dibromo-3(2H)-pyridazone]-α-pivalylacetanilide

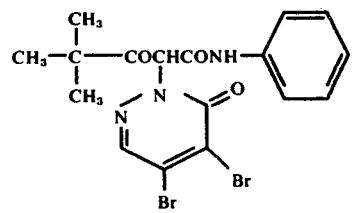

(B-7) α-[6-p-Bromoanilino-3(2H)-pyridazone]-α-pivalylacetanilide

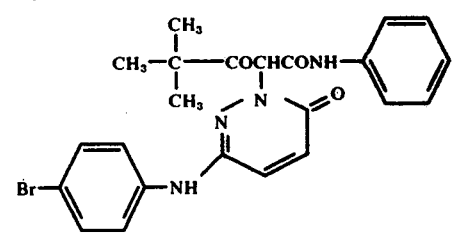

(B-8) α-[4-Chloro-3(2H)-pyridazone]-α-benzoylacetanilide

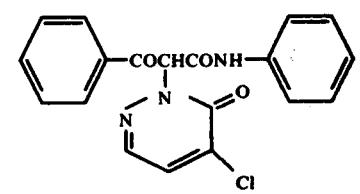

(B-9) α-[4,5-Dibromo-3(2H)-pyridazone]-α-pivalyl-2-chloro-5-[γ-(2,4-di-t-amylphenoxy)-butyramide]-acetanilide

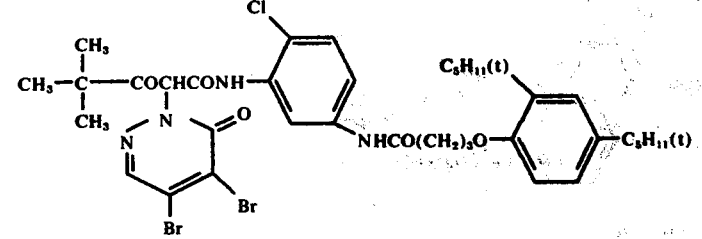

(B-10) α-(p-Octadecyloxybenzoyl)-α-[4,5-dibromo-3(2H)-pyridazone]-3,5-dicarboxyacetanilide dipotassium salt

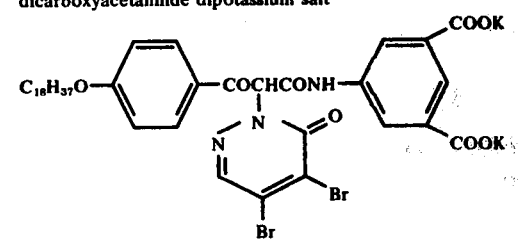

(B-11) α-[5-Bromo-6-phenyl-3(2H)-pyridazone]-α-benzyl-2-chloro-5-[α-(dodecyloxycarbonyl)-ethoxycarbonyl]-acetanilide -continued

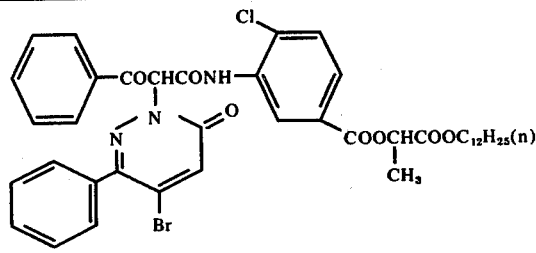

(B-12) α-[4-Methyl-3(2H)-pyridazone]-α-benzoyl-2,5-dichloroacetanilide

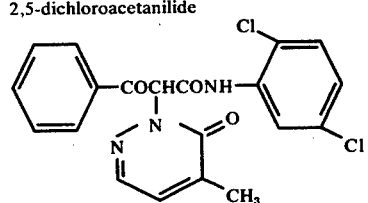

(B-13) α-[6-Ethoxy-3(2H)-pyridazone]-α-pivalylacetanilide

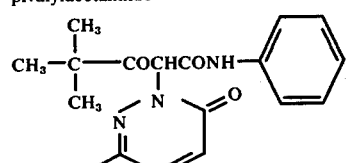

(B-14) α-[4-Methyl-6-chloro-3(2H)-pyridazone]-α-pivalyl-2-chloro-5-[γ-2,4-di-t-amylphenoxy)-butyramide]-acetanilide

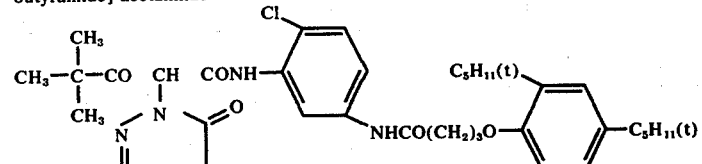

(B-15) α-[6-Octyl-3(2H)-pyridazone]-α-pivalylacetanilide

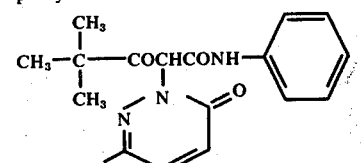

(B-16) α-[6-Phenyl-3(2H)-pyridazone]-α- 3-[α-(2,4-di-t-amylphenoxy)-butyramide]-benzoyl -2-methoxyacetanilide

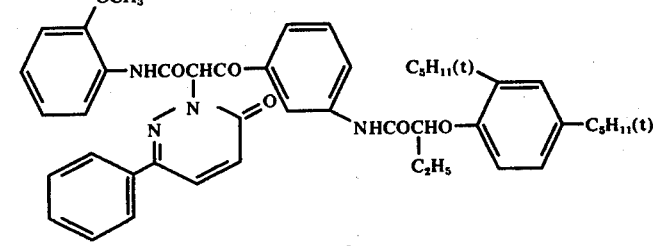

(B-17) α-[4-Chloro-5-amino-3(2H)-pyridazone]-α-benzoylacetanilide

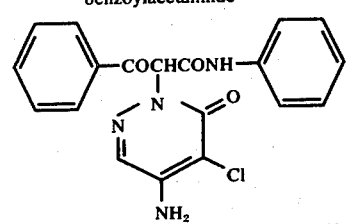

(B-18) α-[4-Acetyl-5,6-diphenyl-3(2H)-pyridazone]-α-benzoylacetanilide

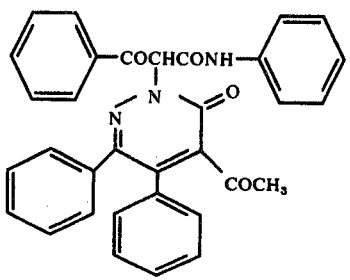

(B-19) α-[4,5-Dichloro-3(2H)-pyridazone]-α-benzoyl-2-chloro-5-[α-(dodecyloxycarbonyl)-ethoxycarbonyl]-acetanilide

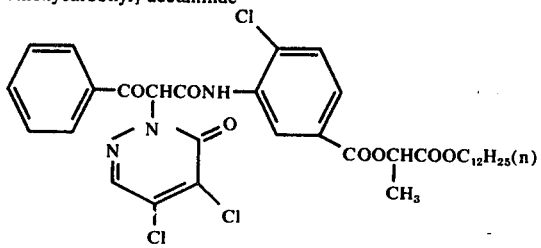

These couplers according to the present invention can be synthesized by, for example, reacting a yellow coupler having an active methylene group, one of the hydrogen atoms of which has been substituted by a halogen atom, with a 2(1H)-pyridone compound (the above-mentioned compound bearing a number prefixed with A) or with a 3(2H)-pyridazone compound (the above-mentioned compound bearing a number prefixed with B).

Typical procedures for synthesizing the couplers according to the present invention are explained in detail below with reference to synthesis examples.

SYNTHESIS EXAMPLE 1

Synthesis of the coupler (A-1):

A mixture comprising 3.0 g. of α-pivalyl-α-bromoacetanilide and 1.4 g. of 2(1H)-pyridone potassium salt was reacted by heating under reflux for 2 hours in 50 ml. of acetonitrile. Thereafter, the reaction liquid was subjected to filtration, and the filtrate was dried under reduced pressure. Subsequently, the residue was recrystallized from alcohol to obtain 2.1 g. of white crystals, m.p. 229°–231°C.

|  | C | H | N |
|---|---|---|---|
| Calculated (%) | 69.21 | 6.45 | 8.97 |
| Found (%) | 69.16 | 6.43 | 9.01 |

SYNTHESIS EXAMPLE 2

Synthesis of the coupler (A-10):

A mixture comprising 2.6 g. of α-benzoyl-α-chloroacetanilide and 2.1 g. of 3-bromo-2(1H)-pyridone, and 50 ml. of acetonitrile were treated in the same manner as in Synthesis Example 1 to obtain 2.3 g. of white crystals, m.p. 141°–143°C.

|  | C | H | N | Br |
|---|---|---|---|---|
| Calculated (%) | 58.41 | 3.68 | 6.81 | 19.43 |
| Found (%) | 58.48 | 3.70 | 6.74 | 19.29 |

SYNTHESIS EXAMPLE 3

Synthesis of the coupler (A-17):

A mixture comprising 6.1 g. of α-pivalyl-α-chloro-2-chloro-5-[γ-(2,4-di-t-amylphenoxy)-butyramide]-acetanilide and 2.1 g. of 5-bromo-2(1H)-pyridone potassium salt was reacted for 3.5 hours in 70 ml. of acetonitrile. After the reaction, the reaction liquid was subjected to filtration, and the filtrate was dried under reduced pressure. Therafter, the residue was dissolved in 100 ml. of ethyl acetate, washed with a 5% aqueous sodium carbonate solution, washed with water and then treated with a 1N-aqueous hydrochloric acid solution. Subsequently, the ethyl acetate layer was concentrated, and the residue was recrystallized from a mixed solvent comprising n-hexane, alcohol and water to obtain 5.1 g. of white crystals, m.p. 158.5°–160.5°C.

|  | C | H | N | Br | Cl |
|---|---|---|---|---|---|
| Calculated (%) | 61.41 | 6.65 | 5.65 | 10.75 | 4.77 |
| Found (%) | 61.39 | 6.66 | 5.71 | 10.43 | 4.84 |

SYNTHESIS EXAMPLE 4

Synthesis of the coupler (A-3):

A mixture comprising 6.1 g. of α-pivalyl-α-chloro-2-chloro-5-[γ-(2,4-di-t-amylphenoxy)-butyramide]-acetanilide and 1.3 g. of 2 (1H)-pyridone potassium salt was treated in the same manner as in Synthesis Example 3, and the resulting residue was recrystallized from a mixed solvent comprising n-hexane and chloroform to obtain 3.2 g. of white crystals, m.p. 140°–142°C.

| Elementary analysis: | C | H | N | Cl |
|---|---|---|---|---|
| Calculated (%) | 68.70 | 7.95 | 6.33 | 5.34 |
| Found (%) | 68.79 | 7.61 | 6.27 | 5.41 |

According to the above-mentioned systhesis procedures, other couplers bearing numbers prefixed with A can be synthesized as well. Elementary analysis values of the thus synthesized couplers are as set forth in the following table:

Elementary analysis values

| Coupler No. | Calculated (%) | | | | | Found (%) | | | | |
|---|---|---|---|---|---|---|---|---|---|---|
| | C | H | N | Cl | Br | C | H | N | Cl | Br |
| (A- 2) | 56.70 | 4.76 | 7.35 | 18.60 | — | 56.64 | 4.77 | 7.31 | 18.54 | — |
| (A- 4) | 65.32 | 7.07 | 6.01 | 10.15 | — | 65.29 | 7.11 | 5.99 | 10.11 | — |
| (A- 5) | 65.49 | 4.12 | 7.63 | 9.67 | — | 65.43 | 4.12 | 7.57 | 9.71 | — |
| (A- 6) | 72.43 | 7.27 | 6.18 | — | — | 72.37 | 7.26 | 6.14 | — | — |
| (A- 7) | 56.86 | 5.96 | 3.32 | — | 9.46 | 56.91 | 5.94 | 3.27 | — | 9.53 |
| (A- 8) | 58.79 | 5.66 | 5.02 | — | 19.08 | 58.80 | 5.66 | 4.99 | — | 19.17 |
| (A- 9) | 67.95 | 7.17 | 8.13 | 5.14 | — | 67.89 | 7.14 | 8.07 | 5.07 | — |
| (A-11) | 61.41 | 6.65 | 5.65 | 4.77 | 10.75 | 61.50 | 6.59 | 5.59 | 4.69 | 10.68 |
| (A-12) | 50.90 | 4.04 | 6.60 | 8.35 | 18.82 | 50.82 | 4.02 | 6.57 | 8.42 | 18.73 |
| (A-13) | 64.90 | 6.38 | 5.54 | — | 10.53 | 64.93 | 6.38 | 5.61 | — | 10.41 |
| (A-14) | 70.56 | 7.11 | 8.23 | — | — | 70.61 | 7.09 | 8.17 | — | — |
| (A-15) | 72.95 | 6.35 | 6.30 | — | — | 73.00 | 6.33 | 6.27 | — | — |
| (A-16) | 65.77 | 6.33 | 5.61 | 9.47 | — | 65.82 | 6.34 | 5.59 | 9.43 | — |
| (A-18) | 73.31 | 5.59 | 7.77 | — | — | 73.33 | 5.60 | 7.81 | — | — |
| (A-19) | 69.91 | 6.80 | 8.58 | — | — | 69.99 | 6.82 | 8.61 | — | — |
| (A-20) | 68.10 | 6.91 | 5.54 | 4.68 | — | 68.16 | 6.89 | 5.51 | 4.72 | — |

SYNTHESIS EXAMPLE 5

Synthesis of the coupler (B-1):

A mixture comprising 5.2 g. of $\alpha$-pivalyl-$\alpha$-chloroacetanilide and 2.9 g. of 3(2H)-pyridazone potassium salt was reacted by heating under reflux for 2 hours in 80 ml. of acetonitrile. After the reaction, the reaction liquid was subjected to filtration, and the filtrate was dried under reduced pressure. Thereafter, the residue was recrystallized from methyl alcohol to obtain white crystals, m.p. 212°–214°C.

| Elementary analysis: | C | H | N |
|---|---|---|---|
| Calculated (%) | 65.16 | 6.11 | 13.41 |
| Found (%) | 65.24 | 6.07 | 13.29 |

SYNTHESIS EXAMPLE 6

Synthesis of the coupler (B-8):

A mixture comprising 5.5 g. of $\alpha$-benzoyl-$\alpha$-chloroacetanilide and 2.6 g. of 4-chloro-3(2H)-pyridazone potassium salt, and 80 ml. of acetonitrile were treated in the same manner as in Synthesis Example 5, and the resulting residue was recrystallized from methyl alcohol to obtain white crystals, m.p. 173°–175°C.

| Elementary analysis: | C | H | N | Cl |
|---|---|---|---|---|
| Calculated (%) | 62.05 | 3.84 | 11.43 | 9.64 |
| Found (%) | 62.01 | 3.87 | 11.40 | 9.71 |

Synthesis Example 7

Synthesis of the coupler (B-5):

A mixture comprising 4.3 g. of $\alpha$-pivalyl-$\alpha$-chloro-2-chloro-5-[$\gamma$-(2,4-di-t-amylphenoxy)-butyramide]-acetanide and 1.5 g. of 4,5-dichloro-3(2H)-pyridazone was reacted by heating under reflux for 2 hours and 45 minutes in 80 ml. of acetonitrile. After the reaction, the reaction liquid was subjected to filtration, and the filtrate was dried under reduced pressure. Subsequently, the residue was dissolved in 100 ml. of ethyl acetate, washed with a 5% aqueous sodium carbonate solution, washed with water, treated with a 1N-aqueous hydrochloric acid solution, and then washed with water. Thereafter, the ethyl acetate layer was concentrated, and the residue was recrystallized from a mixed solvent comprising n-hexane and ethyl alcohol to obtain white crystals, m.p. 183°185°C.

| Elementary analysis: | C | H | N | Cl |
|---|---|---|---|---|
| Calculated (%) | 60.53 | 6.45 | 7.63 | 14.49 |
| Found (%) | 60.57 | 6.43 | 7.57 | 14.41 |

SYNTHESIS EXAMPLE 8

Synthesis of the coupler (B-4):

A mixture comprising 7.4 g. of $\alpha$-benzoyl-$\alpha$-chloro-2-chloro-5-[$\gamma$-(dodecyloxycarbonyl)-ethoxycarbonyl]-acetanilide and 4.0 g. of 4,5-dibromo-3(2H)-pyridazone was reacted by heating under reflux for 3 hours in 100 ml. of acetonitrile. Thereafter, the reaction liquid was treated in the same manner as in Synthesis Example 7, and the resulting residue was recrystallized from a mixed solvent comprising n-hexane and ethyl alcohol to obtain white crystals, m.p. 110°111°C.

| Elementary analysis: | C | H | N | Cl | Br |
|---|---|---|---|---|---|
| Calculated (%) | 51.90 | 4.98 | 5.19 | 4.38 | 19.73 |
| Found (%) | 51.89 | 4.98 | 5.21 | 4.42 | 19.80 |

SYNTHESIS EXAMPLE 9

Synthesis of the coupler (B-9):

A mixture comprising 6.6 g. of $\alpha$-pivalyl-$\alpha$-chloro-2-chloro-5-[$\gamma$-(2,4-di-t-amylphenoxy)-butyramide]-acetanilide and 3.6 g. of 4,5-dibromo-3(2H)-pyridazone potassium salt was treated in the same manner as in Synthesis Example 7, and the resulting residue was recrystallized from a mixed solvent comprising ethyl alcohol and benzene to obtain white crystals, m.p. 185°–188°C.

| Elementary analysis: | C | H | N | Br | Cl |
|---|---|---|---|---|---|
| Calculated (%) | 53.99 | 5.76 | 6.81 | 19.42 | 4.31 |
| Found (%) | 54.03 | 5.74 | 6.79 | 19.35 | 4.27 |

According to the above-mentioned synthesis procedures, other couplers bearing numbers prefixed with B can be synthesized as well. Elementary analysis values of the thus synthesized couplers are set forth in the following table:

Elementary analysis values

| Coupler No. | Calculated (%) | | | | | Found (%) | | | | |
|---|---|---|---|---|---|---|---|---|---|---|
| | C | H | N | Cl | Br | C | H | N | Cl | Br |
| (B- 2) | 68.46 | 4.54 | 12.61 | — | — | 68.51 | 4.55 | 12.58 | — | — |
| (B- 3) | 66.80 | 7.42 | 8.42 | 5.33 | — | 66.73 | 7.41 | 8.39 | 5.24 | — |
| (B- 6) | 43.33 | 3.64 | 8.92 | — | 33.92 | 43.37 | 3.64 | 8.91 | — | 33.87 |
| (B- 7) | 57.15 | 4.80 | 11.59 | — | 16.53 | 57.11 | 4.82 | 11.63 | — | 16.61 |
| (B-10) | 50.70 | 5.13 | 4.55 | — | 17.30 | 50.76 | 5.11 | 4.59 | — | 17.37 |
| (B-11) | 61.00 | 5.62 | 5.21 | 4.39 | 9.90 | 61.05 | 5.61 | 5.17 | 4.45 | 9.89 |
| (B-12) | 56.45 | 3.74 | 10.39 | 17.54 | — | 56.51 | 3.76 | 10.43 | 17.47 | — |
| (B-13) | 63.85 | 6.49 | 11.76 | — | — | 63.91 | 6.51 | 11.73 | — | — |
| (B-14) | 63.94 | 7.06 | 7.85 | 9.94 | — | 64.00 | 7.06 | 7.89 | 9.99 | — |
| (B-15) | 70.50 | 8.29 | 9.87 | — | — | 70.50 | 8.31 | 9.89 | — | — |
| (B-16) | 72.99 | 6.93 | 7.40 | — | — | 73.03 | 6.93 | 7.37 | — | — |
| (B-17) | 59.61 | 3.95 | 14.64 | 9.26 | — | 59.67 | 3.93 | 14.61 | 9.20 | — |
| (B-18) | 75.13 | 4.78 | 7.97 | — | — | 75.07 | 4.80 | 7.91 | — | — |
| (B-19) | 58.30 | 5.59 | 5.83 | 14.75 | — | 58.37 | 5.62 | 5.81 | 14.69 | — |

The thus obtained yellow couplers according to the present invention are useful as the so-called protect dispersed type couplers used in the form of solutions in high boiling organic solvents, e.g. dibutyl phthalate, tricresyl phosphate, etc., which have a boiling point of more than 175° C. and which are difficulty miscible with water. Alternatively, they may be used in the form of solutions not in the above-mentioned high boiling solvents but only in substantially water-insoluble low boiling organic solvents such as ethyl acetate, butyl acetate, etc., or in water-soluble low boiling organic solvents such as methanol, ethanol, methyl isobutyl ketone, etc. Some of the couplers are quite useful as the so-called Fisher's dispersed type couplers which are dispersed by use of alkaline or aqueous solutions.

Further, the yellow couplers according to the present invention are useful as the so-called external couplers of such a type that the couplers are incorporated into developers to form dye images, or as couplers for use in the so-called diffusion transfer method, in which a photosensitive layer and an image-receiving sheet are brought into contact with each other during development to carry out image transfer.

Thus, the yellow couplers according to the present invention may be used to form yellow dye images by adoption of various methods. Further, they have such advantages that even when any method is adopted, the resulting dyes are excellent in spectral absorption characteristics and are quite stable to light, heat and humidity. In case the yellow couplers according to the present invention are incorporated into light-sensitive color photographic materials, the photosensitive layers can be made thinner, with the result that the photographic materials are enhanced in sharpness and improved in developability. In addition, the photographic materials incorporated with the couplers according to the present invention have the advantages that even when the development time is prolonged, they are scarcely increased in fog, and form no such color stains as observed in the case where conventional couplers are used.

As color developing agents which are used in combination with the couplers according to the present invention, there may be used p-aminophenol type developing agents whose amino groups have not been substituted, or phenylenediamine type silver halide developing agents such as, for example, diethyl-p-phenylenediamine hydrochloride, monomethyl-p-phenylenediamine hydrochloride, dimethyl-p-phenylenediamine hydrochloride, 2-amino-5-diethylaminotoluene hydrochloride, 2-amino-5-(N-ethyl-N-dodecyamino)-toluene, N-ethyl-N-β-methanesulfonamidoethyl-3-methyl-4-aminoaniline sulfate, N-ethyl-N-β-methanesulfonamido-ethyl-4-aminoaniline and 4-N-ethyl-N-β-hydroxyethylaminoaniline. Some of the couplers according to the present invention are incorporated into alkaline developers and are used as external couplers, as mentioned previously. Even when the developers used in the above case contain sulfites, carbonates, bisulfites, bromides or iodides of alkali metals, the yellow couplers according to the present invention bring about no detrimental interactions with the compounds contained in the developers.

A typical example of the above-mentioned developers is as follows:

| | |
|---|---|
| 2-Amino-5-diethylaminotoluene hydrochloride | 2.0 g. |
| Anhydrous sodium sulfite | 2.0 g. |
| Anhydrous sodium carbonate | 2.0 g. |
| Potassium bromide | 1.0 g. |
| Yellow coupler (A-1) or (B-6) | 2.0 g. |
| Water to make | 1,000 ml. |

The yellow couplers according to the present invention are applicable to various light-sensitive color photographic materials susceptible to, for example, ultraviolet rays, visible rays, infrared rays, X-rays, γ-rays, or microwave and the like electromagnetic wave energies. For incorporation of the couplers according to the present invention into light-sensitive color photographic emulsions, there may be adopted any of the know procedures. For example, in order to be used as the previously mentioned protect type coupler, one or more of the couplers according to the present invention are dissolved in one or both of at least one high boiling organic solvent having a boiling point of more than 175° C. such as tricresyl phosphate or dibutyl phthalate and at least one low boiling organic solvent such as ethyl acetate or butyl propionate. Subsequently, the resulting solution is mixed with an aqueous gelatin solution containing a surface active agent, and then dispersed by means of a high speed rotary mixer or colloid mill to form a coupler dispersion. The thus formed coupler dispersion is added directly to a silver halide photographic emulsion, which is then coated on a support, followed by drying. Alternatively, the above-mentioned coupler dispersion is set, finely cut, freed from the low boiling solvent by water-washing or the like means, and thereafter added to the photographic emulsion, which is then coated on a support, followed by drying. In this case, it is preferable, in general, to incorporate the coupler according to the present invention in a proportion of 10 to 300 g. per mole of the silver halide, though the proportion may be varied depending on application purposes.

Among the couplers according to the present invention, the couplers (A-4), (A-8), (B-4), (B-5) and (B-16), for example, may be dispersed in photographic emulsions by adoption of the above-mentioned procedure without using high boiling solvents; the couplers (A-7) and (B-10) may be dispersed in an emulsion according to the Fischer's dispersion method; the couplers (A-1), (B-6) and (B-8) may be incorporated into developers; and the coupler (B-15) may be used for diffusion transfer.

The photographic emulsions, which are used in the present invention to form yellow images by use of the yellow couplers according to the present invention, may be prepared by use of various halides such as silver chloride, silver iodobromide, silver chlorobromide, etc. Further, the emulsions may have been subjected to chemical sensitization or to spectral sensitization using carbocyanine dyes or merocyanine dyes, and may have been incorporated with ordinary photographic additives such as, for example, antifoggants, stabilizers, stain-preventing agents, anti-irradiation agents, high polymer additives, coating aids, etc.

Light-sensitive color photographic materials containing the couplers according to the present invention are incorporated with ultraviolet absorbers, whereby the resulting color images can be further enhanced in durability. Color developers used to develop light-sensitive color photographic materials containing the yellow couplers according to the present invention, or color developers containing the yellow couplers according to the present invention, may contain development controlling agents, e.g. citrazinic acid, in addition to the aforesaid developing agents.

The present invention is illustrated in more detail below with reference to examples, but it is needless to say that the scope of the invention is not limited to the examples.

EXAMPLE 1

20.0 Grams of each of the couplers (A-3), (A-17), (B-9), (B-16) and (B-19) was completely dissolved at 60° C. in a mixed solvent comprising 20 ml. of dibutyl phthalate and 60 ml. of ethyl acetate. The resulting solution was mixed with 10 ml. of a 6% aqueous solution of Alkanol B (alkylnaphthalenesulfonate produced by DuPont) and with 200 ml. of a 6% aqueous gelatin solution, and the mixture was dispersed by means of a colloid mill to form a coupler dispersion. This coupler dispersion was added to 1 kg. of a high sensitivity silver iodobromide emulsion, which was then coated on a film base and dried to obtain a light-sensitive photographic material having a stable film coating. The thus obtained photographic material was exposed according to an ordinary procedure and then developed at 20° C. for 10 minutes with a developer of the following composition:

| | |
|---|---|
| N-Ethyl-N-β-methanesulfonamidoethyl-3-methyl-4-aminoaniline hydrochloride | 5.0 g. |
| Anhydrous sodium sulfite | 2.0 g. |
| Benzyl alcohol | 3.8 g. |
| Sodium carbonate (monohydrate) | 50.0 g. |
| Potassium bromide | 1.0 g. |
| Sodium hydroxide | 0.55 g. |
| Water to make | 1,000 ml. |

Subsequently, the developed photographic material was subjected to ordinary stop-fixing, water-washing, bleaching, water-washing, fixing, water-washing and stabilization treatments.

Each sample obtained in the above manner was measured in absorption maximum (λ-max), maximum density (D-max) and storability of yellow image.

For comparison, control samples were prepared in the same manner as above, except that the couplers used were unsubstituted type couplers identical in matrix structure with the couplers used in the above, and were also measured in such photographic properties as mentioned above.

The results obtained were as set forth in Table 1.

Table 1

| Sample No. | Coupler | λ-max | D-max | Yellow image Ratio of residual dye (%) Light fastness | Humidity fastness |
|---|---|---|---|---|---|
| 1 | Unsubstituted type coupler identical in structure with the coupler (A-3) | 448 | 1.21 | 97 | 99 |
| 2 | Coupler (A-3) | 448 | 1.99 | 97 | 99 |
| 3 | Unsubstituted type coupler identical in structure with the coupler (A-17) | 448 | 1.22 | 97 | 99 |
| 4 | Coupler (A-17) | 448 | 2.10 | 98 | 99 |
| 5 | Unsubstituted type coupler identical in structure with the coupler (B-9) | 447 | 1.52 | 96 | 99 |
| 6 | Coupler (B-9) | 447 | 1.91 | 96 | 100 |
| 7 | Unsubstituted type coupler identical in structure with the coupler (B-16) | 453 | 1.86 | 74 | 96 |
| 8 | Coupler (B-16) | 453 | 2.43 | 75 | 98 |
| 9 | Unsubstituted type coupler identical in structure with the coupler (B-19) | 453 | 1.86 | 74 | 96 |
| 10 | Coupler (B-19) | 453 | 2.73 | 74 | 99 |

λ-max: Spectral absorption maximum wavelength (mμ)

D-max: Maximum density

Ratio of residual dye: Ratio (%) of dye left after subjecting a portion having an initial density of 1.0 to the following treatments:

Treatments:

Light fastness: Exposed to xenon arc lamp at 50° C. for 30 hours.

Humidity fastness: Allowed to stand at 50° C. and RH 80% for 7 days.

From Table 1, it is understood that the yellow couplers according to the present invention provide excellent properties and are quite useful as photographic yellow couplers for use in multi-layered polychromatic photographic materials.

EXAMPLE 2

Each of the couplers (A-11), (B-4) and (B-5) was added in the same manner as in Example 1 to a gelatin silver iodobromide emulsion. The amount of silver halide used in this case was identical with that in Example 1. Subsequently, the emulsion was treated in the same manner as in Example 1 to prepare photographic materials.

For comparison, photographic materials were prepared in the same manner as above, except that the couplers used were unsubstituted type couplers identical in structure with the above-mentioned couplers.

The thus prepared photographic materials were exposed and then developed with the same developer as in Example 1 to obtain samples. These samples were individually measured by means of a densitometer in density of yellow dye to blue light at each stage. The results obtained were plotted to obtain the graph as shown in the accompanying drawings, in which the horizontal axis shows the exposure amount (log E) and the vertical axis shows the density. In FIG. 1, the curve 1 shows the case where the 4-equivalent coupler was used; the curve 2 shows the case where the coupler (A-11) according to the present invention was used; in FIG. 2 the curves 3 and 4 show, respectively, the cases where an unsubstituted type coupler identical in structure with the coupler (B-4) and an unsubstituted type coupler identical in structure with the coupler (B-5) were used; and the curves 5 and 6 show, respectively, the cases where the couplers (B-4) and (B-5) according to the present invention were used.

As is clear from the drawing, the couplers according to the present invention can be successfully used even when silver is used in one half the amount required in the prior art.

EXAMPLE 3

Each of the couplers (A-7) and (B-10) was dispersed in a mixed solvent comprising ethanol and water, and then dissolved by addition of a 10% aqueous sodium hydroxide solution. The resulting solution was mixed with a gelatin solution containing 12% of gelatin and 5.13% of Alkanol B, and then neutralized with acetic acid. The neutralized liquid was dispersed in a silver iodobromide emulsion, which was then coated on a support and dried to obtain a photographic material. This photographic material was subjected to ordinary exposure, developed at 20° C. for 10 minutes with the same developer as in Example 1, and then subjected to 3-step bath treatments comprising bleach-fixing, water-washing and stabilization to prepare samples.

For comparison, control samples were prepared in the same manner as above, except that the couplers used were identical in structure with the couplers (A-7) and (B-10).

These samples were individually measured in fog, λ-max and D-max to obtain the results as set forth in Table 2.

Table 2

| Sample No. | Coupler | Fog | λ-max | D-max |
|---|---|---|---|---|
| 11 | Coupler (A-7) | 0.14 | 450 | 2.21 |
| 12 | Unsubstituted type coupler identical in structure with the coupler (A-7) | 0.15 | 450 | 1.86 |
| 13 | Coupler (B-10) | 0.19 | 450 | 2.67 |
| 14 | Unsubstituted type coupler identical in structure with the coupler (B-10) | 0.14 | 450 | 1.85 |

As is clear from Table 2, it is understood that even when the Fischer's dispersion method is adopted, the yellow couplers according to the present invention provide excellent photographic properties.

EXAMPLE 4

Photographic materials containing an ordinary silver iodobromide emulsion were individually exposed and then subjected to color development using a color developer of the composition shown below which contained each of the couplers (A-1), (B-6) and (B-8) and unsubstituted type couplers identical in structure with said couplers.

| Composition of developer: | |
|---|---|
| 2-Amino-5-diethylaminotoluene hydrochloride | 2.0 g. |
| Anhydrous sodium sulfite | 2.0 g. |
| Anhydrous sodium carbonate | 20.0 g. |
| Potassium bromide | 1.0 g. |
| Coupler | 2.0 g. |
| Water to make | 1,000 ml. |

Each sample obtained in the above manner was measured in fog, λ-max and D-max to obtain the results as set forth in Table 3.

Table 3

| Sample No. | Coupler | Fog | λ-max | D-max |
|---|---|---|---|---|
| 15 | Coupler (A-1) | 0.07 | 443 | 2.13 |
| 16 | Unsubstituted type coupler identical in structure with the coupler (A-1) | 0.04 | 443 | 1.42 |
| 17 | Coupler (B-6) | 0.11 | 443 | 1.86 |
| 18 | Unsubstituted type coupler identical in structure with the coupler (B-6) | 0.07 | 442 | 1.45 |
| 19 | Coupler (B-8) | 0.09 | 452 | 2.65 |
| 20 | Unsubstituted type coupler identical in structure with the coupler (B-8) | 0.05 | 452 | 1.72 |

From Table 3, it is understood that the couplers according to the present invention are quite useful as external couplers, as well.

EXAMPLE 5

A silver iodobromide emulsion incorporated with the coupler (B-15) was coated on a paper and then dried to prepare a photographic material. This photographic material was subjected to image-wise exposure, developed with an alkaline developer (pH 13) containing, per liter, 2 g. of sodium sulfite and 11 g. of 4-N-ethyl-N-β-hydroxyethylaminoaniline, and then closely contacted at 24° C. for 3 minutes with an image-receiving sheet containing dimethyl-β-hydroxyethyl-γ-stearamidopropyl ammonium dihydrogen phosphate as a mordanting agent. Subsequently, the image-receiving sheet was peeled off from the photographic material to obtain an excellent positive image of yellow dye derived from diffusion transfer onto the image-receiving sheet of a yellow dye, which had been formed due to the aforesaid development.

What we claim is:

1. A light-sensitive gelatinous silver halide photographic emulsion containing a substituted type photographic yellow coupler having the formula,

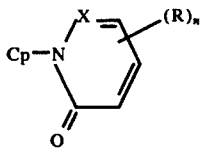

wherein X is a —N= or —Ch= group; Cp is a residue formed by removing one hydrogen atom of the active methylene group of a yellow coupler of the acetanilide type; n is an integer of 1 to 4; and R is a hydrogen or halogen atom, or an alkyl, alkoxy, alkycarbonyl, aryl, arylcarbonyl, amino, acylamino, carboxyl, nitrile, aralkyl or aralkyloxy group, provided that in case n is 2 or more the R groups may be the same or different and two adjacent R groups in combination may form a benzene ring.

2. A light-sensitive gelatinous silver halide photographic emulsion containing a substituted type photographic yellow coupler having the formula,

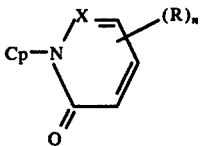

wherein X is a —N= or —CH= group; Cp is a residue formed by removing one hydrogen atom of the active methylene group of a yellow coupler of the acylacetanilide type; n is an integer of 1 to 4; and R is a hydrogen or halogen atom, or an alkyl, alkoxy, alkycarbonyl, aryl, arylcarbonyl, amino, acylamino, carboxyl, nitrile, aralkyl or aralkyloxy group, provided that in case n is 2 or more the R groups may be the same or different, and two adjacent R groups in combination may form a benzene ring.

3. A light-sensitive gelatinous silver halide photographic emulsion as claimed in claim 2 wherein the X is a —CH= group.

4. A light-sensitive gelatinous silver halide photographic emulsion as claimed in claim 2 wherein the X is a —N= group.

5. A light-sensitive gelatinous silver halide photographic emulsion containing a substituted type photographic yellow coupler having the formula,

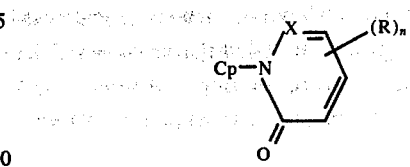

wherein X is a —N= or —CH= group; Cp is a residue formed by removing one hydrogen atom of the active methylene group of a yellow coupler of the α-pivalylacetanilide or α-benzoylacetanilide type; n is an integer of 1 to 4; and R is a hydrogen or halogen atom, or an alkyl, alkoxy, alkycarbonyl, aryl, arylcarbonyl, amino, acylamino, carboxyl, nitrile, aralkyl or aralkyloxy group, provided that in case n is 2 or more the R groups may be the same or different, and two adjacent R groups in combination may form a benzene ring.

6. A method of forming a yellow dye image which comprises bringing a yellow coupler into contact with exposed silver halide crystals in the presence of an aromatic amine type developing agent to form a yellow dye image wherein said yellow coupler has the formula,

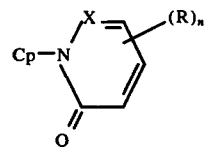

wherein X is a —N= or —CH= group; Cp is a residue formed by removing one hydrogen atom of the active methylene group of a yellow coupler of the acetanilide type; n is an integer of 1 to 4; and R is a hydrogen or halogen atom, or an alkyl, alkoxy, alkylcarbonyl, aryl, arylcarbonyl, amino, acylamino, carboxyl, nitrile, aralkyl or aralkyloxy group, provided that in case n is 2 or more, the R groups may be the same or different, and two adjacent R groups in combination may form a benzene ring.

7. A method as claimed in claim 6 wherein the Cp is a residue formed by removing one hydrogen atom of the active methylene group of a yellow coupler of the acylacetanilide type.

8. A method as claimed in claim 6 wherein the Cp is a residue formed by removing one hydrogen atom of the active methylene group of a yellow coupler of the α-pivalylacetanilide or α-benzoylacetanilide type.

9. A color developer for developing exposed silver halide crystals, which comprises an aromatic amine type developing agent and a yellow coupler of the formula,

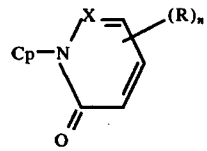

wherein X is a —N= or —CH= group; Cp is a residue formed by removing one hydrogen atom of the active methylene group of a yellow coupler of the acetanilide type; n is an integer of 1 to 4; and R is a hydrogen or halogen atom, or an alkyl, alkoxy, alkylcarbonyl, aryl, arylcarbonyl, amino, acylamino, carboxyl, nitrile, aralkyl or aralkyloxy group, provided that in case n is 2 or more the R groups may be the same or different, and two adjacent R groups in combination may form a benzene ring.

10. A color developer as claimed in claim 9 wherein the Cp is a residue formed by removing one hydrogen atom of the active methylene group of a yellow coupler of the acylacetanilide type.

11. A color developer as claimed in claim 9 wherein the Cp is a residue formed by removing one hydrogen atom of the active methylene group of a yellow coupler of the α-pivalylacetanilide or α-benzoylacetanilide type.

* * * * *